US00PP19053P2

(12) United States Plant Patent
Giesen

(10) Patent No.: US PP19,053 P2
(45) Date of Patent: Jul. 29, 2008

(54) ***LOBELIA* PLANT NAMED 'TECH HEWHIT'**

(50) Latin Name: *Lobelia erinus*
Varietal Denomination: Tech Hewhit

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/732,440

(22) Filed: Apr. 3, 2007

(51) Int. Cl.
*A01H 5/00* (2006.01)

(52) U.S. Cl. ..... Plt./451
(58) Field of Classification Search ..... Plt./451, Plt./263
See application file for complete search history.

*Primary Examiner*—Kent L Bell
*Assistant Examiner*—S. B. McCormick-Ewoldt
(74) *Attorney, Agent, or Firm*—Jondle & Associates, P.C.

(57) ABSTRACT

A new *Lobelia* plant particularly distinguished by its low mounded, pendulous and semi-compact form, vigorous plant habit, dense and free branching, short internodes, large, white flowers and tolerance to heat is disclosed.

2 Drawing Sheets

Genus and species: *Lobelia erinus.*
Variety denomination: 'Tech Hewhit'.

BACKGROUND OF THE NEW PLANT

The present invention comprises a new and distinct cultivar of *Lobelia,* botanically known as *Lobelia erinus,* and hereinafter referred to by the cultivar name 'Tech Hewhit'. The new cultivar originated from a hybridization made in January 2002 in Andijk, The Netherlands. The female parent was 'LOB03-117-1' a white proprietary *Lobelia* line (unpatented), while the male parent was 'LOB02-14-3', a white proprietary *Lobelia* line (unpatented).

The seeds produced by the pollination were sown in March 2003. A single plant selection was chosen for further evaluation and for asexual propagation in July 2003.

The new cultivar was created in 2002 and has been asexually reproduced repeatedly by vegetative cuttings and tissue culture in Gilroy, Calif., and Andijk, The Netherlands over a three and a half year period. The plant was also been trialed at Gilroy, Calif., Andijk, The Netherlands and Hillscheid Germany. The present invention has been found to retain its distinctive characteristics through successive asexual propagations.

Plant Breeder's Rights for this cultivar have been applied for with the European Union on Nov. 13, 2006.

SUMMARY OF THE INVENTION

The following are the most outstanding and distinguishing characteristics of this new cultivar when grown under normal horticultural practices in Gilroy, Calif., and Andijk, The Netherlands.

1. Low mounded, pendulous and semi-compact form;
2. Vigorous plant habit;
3. Dense and free branching;
4. Short internodes;
5. Large, white flowers; and
6. Tolerance to heat.

DESCRIPTION OF PHOTOGRAPHS

This new *Lobelia* plant is illustrated by the accompanying photographs which show overall plant habit including blooms, buds, and foliage of the plant. The colors shown are as true as can be reasonably obtained by conventional photographic procedures.

Figure 1:
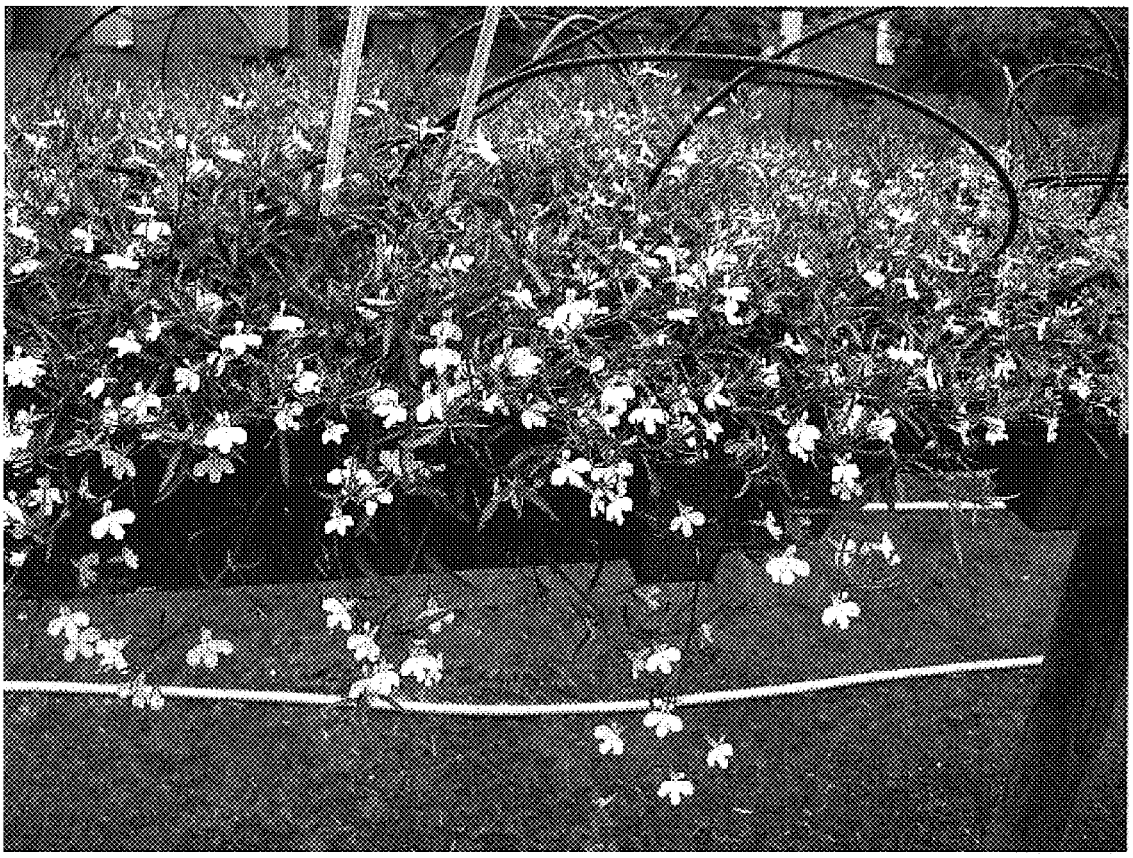

FIG. 1. shows the overall plant habit of the plant at 20 to 23 weeks old, including blooms, buds and foliage, in a flowers box grown in a greenhouse during the late spring before being moved to an outdoors setting during the summer in Andijk, The Netherlands.

Figure 2:
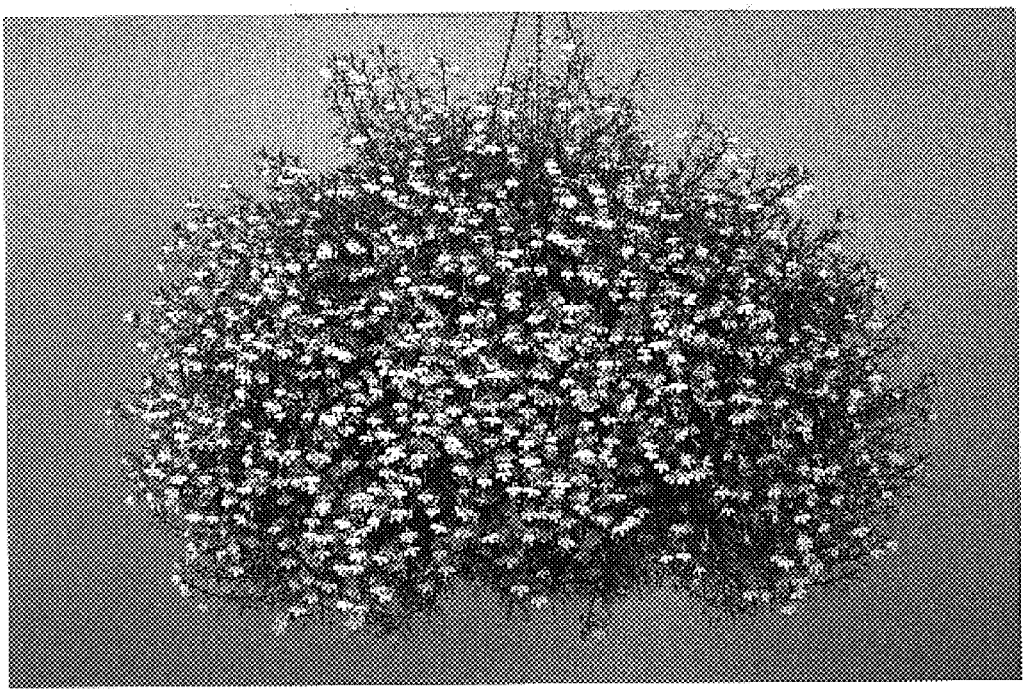

FIG. 2. shows the overall plant habit of 20 weeks old plants, including blooms, buds and foliage of plants in a hanging basket grown outdoors in Hillscheid, Germany.

Figure 3:
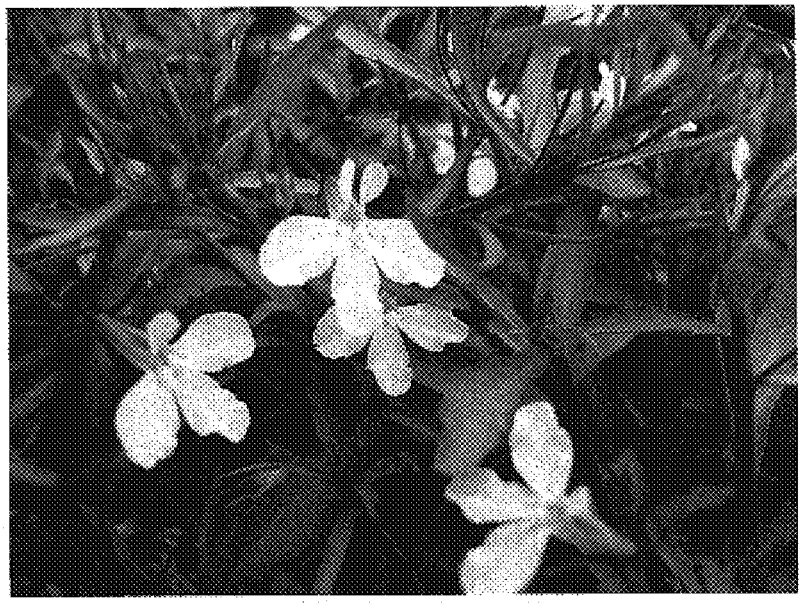

FIG. 3. shows a close-up of the plant at 20 to 23 weeks old, including blooms, buds and foliage, grown in a greenhouse during the late spring before being moved to an outdoors setting during the summer in Andijk, The Netherlands.

DESCRIPTION OF THE NEW CULTIVAR

The following detailed descriptions set forth the distinctive characteristics of 'Tech Hewhit'. The data which define these characteristics were collected in the fall and winter season from 22 to 23 weeks old plants grown in 6-inch pots in Gilroy, Calif. The plants had one plant growth regulator treatment and one terminal pinch at the onset of the trial. Color readings were taken in a greenhouse in January under natural light. Color references are primarily in the R.H.S. Colour Chart of The Royal Horticultural Society of London (R.H.S.) (2001 edition). Texture description details were observed under a dissecting microscope.

DETAILED BOTANICAL DESCRIPTION

Classification:
*Botanical.*—*Lobelia erinus.*
*Common name.*—Lobelia.
Parentage:
*Female parent.*—'LOB03-117-1' proprietary *Lobelia* line (unpatented).

*Male parent.*—'LOB02-14-3' proprietary *Lobelia* line (unpatented).

Growth:

*Growth and branching habit.*—Good vigorous habit, very dense and freely branched; exhibits some heat tolerance.

*Form.*—Herbaceous annual; low mounding, pendulous and semi-compact Height (measured from the top of the soil, including any flowers): 20.0 cm to 24.0 cm.

*Width (horizontal plant diameter, including any flowers).*—50.0 cm to 70.0 cm.

*Time to produce a finished flowering plant.*—9 to 11 weeks for a 6-inch pot.

*Outdoor plant performance.*—Patio planters in mixed container plantings or garden beds.

*Time to initiate roots.*—21 to 28 days at 68 to 74 degrees Fahrenheit.

*Root description.*—Fibrous, freely-branching, and white.

Leaves:

*Arrangement.*—Alternate.

*Color.*—Immature leaf: Upper surface: Closest to RHS 137B. Lower surface: Closest to RHS 137D. Mature leaf: Upper surface: Darker than RHS 137A. Lower surface: RHS 137D; some anthocyanin, about RHS 176B in varying size blotches.

*Length.*—2.7 cm to 5.3 cm.

*Width.*—1.3 cm to 2.2 cm.

*Shape.*—Oblanceolate to obovate.

*Margin.*—Slightly serrate.

*Apex.*—Obtuse.

*Base.*—Cuneate.

*Texture.*—Pilose.

*Venation.*—Pinnate.

*Venation color.*—RHS 144B.

Stems:

*Length.*—50.0 cm to 60.0 cm.

*Diameter.*—0.2 cm.

*Internode length.*—2.0 cm to 3.5 cm.

*Color.*—RHS 137A.

*Texture.*—Pilose.

*Stem anthocyanin.*—Slightly in longitudinal stripes and a little heavier at the axis.

*Peduncle.*—Color: RHS 137A. Length: 2.3 cm to 3.8 cm. Diameter: 0.75 cm. Texture: Pilose.

Flower buds:

*Shape.*—Oblong.

*Diameter.*—0.4 cm to 0.5 cm.

*Length.*—1.3 cm to 1.5 cm.

*Color when bud is first starting to open.*—RHS 1D.

Inflorescence:

*Blooming habit.*—Plants flower freely and continuous in the growing season from spring to the fall.

*Lastingness of individual blooms on plant.*—4 to 8 days depending on environmental conditions.

*Fragrance.*—None.

*Inflorescence type.*—Flowers form at apical axils, with one flower per axil; flowers are labiate; upper petal has two small lobes and lower lip has three larger and broader lobes; lobes are fused at the base.

*Quantity of flowers and buds per flowering branch.*—15 to 20.

Flowers:

*Flower diameter (horizontal).*—2.1 cm to 2.3 cm.

*Flower height (vertical).*—2.0 cm to 2.2 cm.

*Immature flower.*—Color: All lobes: RHS N155B but more white; with a very slight hint of 'pink' in the background.

*Mature flower.*—Upper lobe. Color: Both surfaces: RHS N155B but more white; with a very slightly hint of 'pink' in the background. Length: 0.7 cm. Width: 0.3 cm. Shape: Oblanceolate to obovate. Apex: Abruptly acute. Margin: Entire. Texture: Upper surface: Papillose. Lower surface: Papillose; pilose. Lower lobes: Both surfaces: RHS N155B but more white; with a very slight hint of 'pink' in the background. Length: 2.2 cm to 2.3 cm. Width: 0.6 cm to 0.7 cm. Shape: Mucronulate. Apex: Mucronulate. Margin: Entire. Texture: Upper surface: Papillose. Lower surface: Papillose; pilose.

*Corolla.*—Color: Inside: RHS N155B but more white; very small spots of RHS N80D; 2 basal bars of RHS 5A. Outside: RHS N155B but more white; very slight hint of between RHS 80B and RHS 80C. Tube length: 0.9 cm to 1.0 cm. Diameter: 0.5 cm at the throat; 0.25 at the base.

*Calyx.*—Five sepals with fused bases that curve out and away from the corolla. Color, both surfaces: RHS 137A. Length: 0.9 cm to 1.0 cm. Diameter: 0.1 cm. Shape: Linear. Apex: Acuminate. Texture, both surfaces: Pilose.

Reproductive organs:

*Androecium.*—Number of anthers: 5 fused around the stigma. Filament length: 0.7 cm. Filament color: RHS N155B but more white; very slight hint of RHS N80C. Pollen color: RHS 5D. Pollen amount: Sparse.

*Gynoecium.*—Pistil length: 1.0 cm. Stigma color: RHS N80C but a little lighter. Style color: RHS 144C. Style length: 0.8 cm.

Fruit and Seed Set: Has not been observed.

Disease and Insect Resistance: Resistance and susceptibility is typical of the species.

COMPARISON WITH KNOWN CULTIVARS

'Tech Hewhit' differs from the female parent, 'LOB03-117-1', proprietary breeding line (unpatented), in that 'Tech Hewhit' has longer and thicker stems than 'LOB03-117-1'. Additionally, 'Tech Hewhit' has better plant vigor, darker leaves and larger flowers than 'LOB03-117-1'.

'Tech Hewhit' differs from the male parent, 'LOB02-14-3', proprietary breeding line (unpatented), in that 'Tech Hewhit' has a more trailing plant habit. Additionally, 'Tech Hewhit' has darker leaves and longer, thicker stems than 'LOB02-14-2'.

'Tech Hewhit' differs from the commercial variety 'Kielowa' (U.S. Plant Pat. No. 15,681) in that 'Tech Hewhit' is a little taller plant with shorter internodes and darker green stems and leaves than 'Kielowa'. Additionally, 'Tech Hewhit' has a shorter corolla tube and longer sepals than 'Kielowa'.

I claim:

1. A new and distinct *Lobelia* plant as shown and described herein.

* * * * *